United States Patent [19]

Volk

[11] Patent Number: 5,046,836
[45] Date of Patent: Sep. 10, 1991

[54] DIAGNOSTIC INDIRECT OPHTHMALMOSCOPY CONTACT LENS SYSTEM

[76] Inventor: Donald A. Volk, 9378 Jackson, Mentor, Ohio 44060

[21] Appl. No.: 428,504

[22] Filed: Oct. 27, 1989

[51] Int. Cl.$^5$ .............................................. A61B 3/00
[52] U.S. Cl. .................................... 351/219; 351/205
[58] Field of Search ............ 351/219, 432, 205, 160 R

[56] References Cited

U.S. PATENT DOCUMENTS 4,410,245  10/1983  Koester ............................. 351/219
4,728,183  3/1988  Heacock et al. ..................... 351/219

Primary Examiner—Paul M. Dzierzynski
Attorney, Agent, or Firm—Oldham & Oldham Company

[57] ABSTRACT

A compound diagnostic indirect ophthalmoscopy contact lens utilized for illumination and observation of the fundus of the eye including a plus powered meniscus aspheric contact element and a biconvex aspheric anterior element, each of the lens elements contributing positive refractive power to the optical system and co-acting to illuminate and form an aerial image of the fundus of the eye.

20 Claims, 2 Drawing Sheets

FIG 1
FIG 2
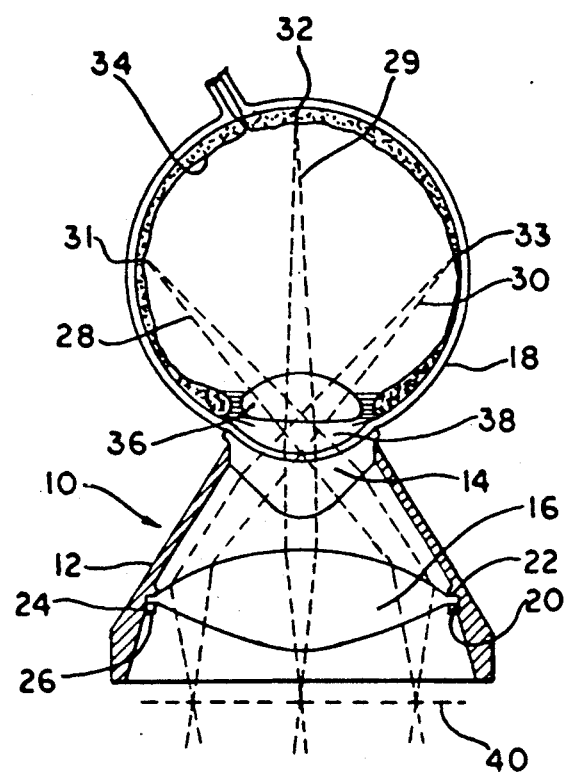
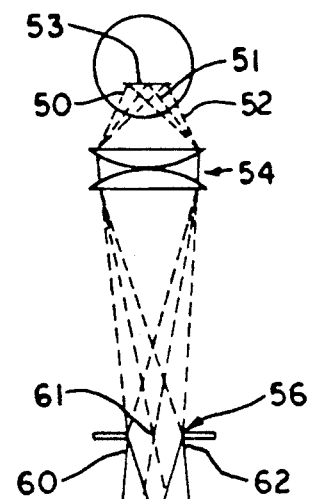
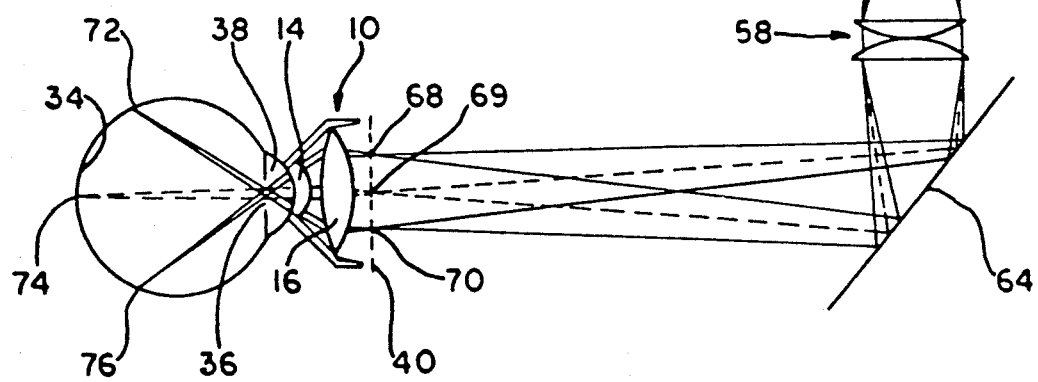

DIAGNOSTIC INDIRECT OPHTHMALMOSCOPY CONTACT LENS SYSTEM

BACKGROUND OF THE INVENTION

The present invention relates to a diagnostic indirect ophthalmoscopy contact lens device. More particularly, the invention relates to a diagnostic contact lens for indirect ophthalmoscopy which operates both as an improved condensing lens device for conveyance of a light through the pupil and onto the fundus of an examined eye as well as for forming a aberration free and extremely wide field inverted real aerial image of the fundus of the eye.

Diagnostic lenses for indirect ophthalmoscopy are used by ophthalmologists and optometrists to observe the fundus of an eye for diagnostic or surgical procedures. Various known ophthalmoscopic lenses or other diagnostic devices, have lenses for conveying light from a source onto the fundus of an eye and forming an aerial image of the fundus. In U.S. Pat. No. 3,954,329, there is shown an ophthalmoscope for viewing a fundus which includes a contact lens which directly contacts the cornea of the eye as well as a posterior or field lens spaced from the contact lens and supported in a housing relative thereto. This invention employs both direct illumination of the fundus of the eye as well as transillumination to obtain wide angle viewing of the fundus. Other similar systems in U.S. Pat. Nos. 4,265,519 and 3,994,341 show various illumination techniques and lens systems for ophthalmoscopes and fundus cameras.

More recently, indirect ophthalmoscopy has been utilized in laser microsurgery techniques to enable the ophthalmologists to obtain a wide angle image of the fundus as well as to convey the laser beam to the fundus accurately. In an attempt to provide wide angle viewing of the fundus without aberration, U.S. Pat. No. 4,728,182 to Heacock utilizes a contact lens element situated relative to an entry lens in a holder. It is stated that the contact lens element is designed such that the light rays emerging from the patient's eye exit the contact lens in a parallel relationship which are then directed to the entry lens. The entry lens is an aspheric lens which forms an aerial image of the fundus.

This patent thus describes an ophthalmic lens system wherein the contact lens has two spherical surfaces, designed such that light rays emerging from the patient's eye and through the contact lens are substantially parallel, rather than convergent, as they exit in an anterior direction from the contact lens. In this design, the aspheric entry lens of this invention will be inadequate in some circumstances as an image forming lens as it will be insufficient for correcting field curvature and aberrations due in part to the spherical design of the contact lens. The contact lens design has failed to account for the corrective quality of the aspheric cornea of the eye itself and may tend to degrade the image of the fundus of the eye.

It is also desired to form an extremely wide field image of the fundus of the eye using a diagnostic contact lens system to enable the ophthalmologist and optometrist to view more of the fundus for proper and easier diagnosis. In the invention of Heacock as well as other prior art inventions, mirrors are sometimes interposed between the contact lens and entry lens of the system to increase the field of view of the fundus. The addition of mirrors into the system adds complexity, costs and may tend to degrade the quality of the image. Even with the use of mirrors it may still be necessary to move the lens on the examined eye.

In a similar manner, the indirect ophthalmoscopy diagnostic contact lens system should function as a condensing lens for converging light from the light source of a biomicroscope through the pupil of an examined eye onto the fundus of the eye. In order to obtain an aberration free, focused image of the light source, such as in a slit lamp biomicroscope or other ophthalmoscope, the lens system should provide the optical properties to avoid aberrations normally associated with spherical lenses.

SUMMARY OF THE INVENTION

There has therefore been found a need to provide a diagnostic contact lens for indirect ophthalmoscopy which has superior optical performance and produces an extremely wide field of view and is substantially free of aberrations. The lens system should function both as an improved condensing lens converging light from a light source and for forming a clear and focused image of the fundus of the eye.

It is therefore a main object of the present invention to provide a diagnostic indirect ophthalmoscopy contact lens which corrects optical aberrations or distortions relating to its functioning simultaneously as an improved condensing lens system for converging light from a biomicroscope light source onto the fundus of an examined eye as well as an improved image forming lens for the fundus of the eye.

It is another object of this invention to provide a diagnostic indirect ophthalmoscopy contact lens utilizing two aspheric optical elements of positive refractive power.

It is another object of this invention to provide a diagnostic indirect ophthalmoscopy contact lens producing an extremely wide field of view of the fundus of the eye.

It is another object of this invention to provide a biconvex aspheric anterior lens element for correction of optical aberrations degrading the aerial image of the fundus.

It is another object of this invention to provide a biconvex aspheric anterior lens element for correction of optical aberrations degrading the image of the aperture of the light source of a biomicroscope projected by the lens of this invention onto the fundus of any eye.

It is another object of this invention to provide within an aspheric anterior surface of a contact element means for correction of optical aberrations degrading the aerial image of the fundus.

It is another object of this invention to provide within an aspheric anterior surface of a contact element means for correction of optical aberrations degrading the image of the aperture of the light source of a biomicroscope projected by the lens of this invention onto the fundus of an eye.

It is another object of this invention to provide an aspheric anterior surface on an aspheric contact element enabling utilization of very short apical radii.

It is another object of this invention to provide an aspheric anterior surface on an aspheric contact element enabling utilization of relatively large diameters.

It is another object of this invention to provide an aspheric posterior surface on an aspheric contact element and means for facilitating translational movement of the lens of this invention on the cornea of an eye under examination.

It is another object of this invention to provide means for securing and interconnecting the posterior and anterior lens elements relative to one another within an easily manipulatable generally conically shaped housing.

It is another object of this invention to provide means for laser delivery to the far peripheral as well as the central fundus of an examined eye.

The objects of the invention are accomplished by an improved diagnostic contact lens for indirect ophthalmoscopy which simultaneously functions as both an improved condensing lens as well as an improved image forming lens. The lens system acts to converge light from the source of a slit lamp biomicroscope or other microscope through the pupil of an examined eye, projecting a distortion free, clear and focused image of the aperture of the light source on to the fundus of an examined eye. The lens system also produces an extremely wide field inverted real aerial image of the fundus of the eye which is essentially free of field curvature, lateral astigmatism and distortion, viewed either monocularly or binocularly through a biomicroscope.

The preferred embodiment of the invention includes an aspheric corneal contact element of positive refractive power, a high powered biconvex aspheric anterior lens, and a generally conically shaped housing securing and interconnecting both lens components while preventing extraneous light, moisture, and dirt from entering the interior optical area. The contact element includes an aspheric anterior surface of the contact element that not only contributes to the improved optical performance of the unit as both a condensing lens and image forming lens, but in addition, because of the continuous and progressive reduction in curvature peripheralward, allows for surfaces with both short apical radii and relatively large diameters. The concave posterior surface of the contact element may also be aspheric, thereby, facilitating an improved corneal fit as well as translateral movement of the lens unit on the eye. The biconvex aspheric anterior element is aspherically shaped to co-act with the aspheric contact element in such a way as to provide optimum condensing and image forming properties. It is desired that each of the two lens elements have significant light converging properties and be aspheric, and it is these features in addition to others that distinguish it from the prior art lenses and which provide improved performance and high optical resolution.

BRIEF DESCRIPTION OF THE DRAWINGS

The objects and advantages of the invention will become apparent as the detailed description of the invention proceeds with reference to the accompanying drawings, wherein;

FIG. 1 is a schematic plan view of the indirect v ophthalmoscopy diagnostic contact lens system of the invention;

FIG. 2 is a schematic plan view of the light path from a light source of a biomicroscope through the lens system of the invention onto the examined eye;

DETAILED DESCRIPTION OF THE INVENTION

Figure 3:
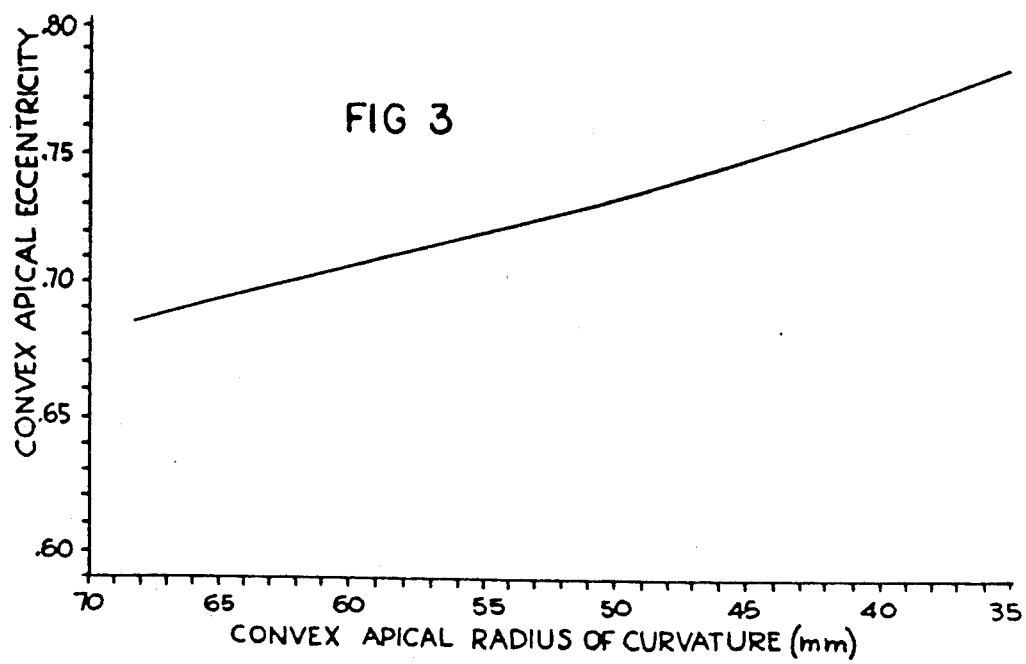
FIG. 3 is a plot of the convex apical eccentricity to the convex apical radius of curvature for the lens elements of the system.

Referring now to FIG. 1, the compound diagnostic indirect ophthalmoscopy contact lens 10 includes a generally conically shaped lens holder 12, providing means for securing and interconnecting the aspheric contact element 14 and the biconvex aspheric anterior element 16. The lens holder 12 also allows a means for digital manipulation of the unit when disposed against the eye 18 of the patient. Both the aspheric contact element 14 and the biconvex aspheric anterior element 16 may be made of homogenous transparent optical material, such as glass or plastic. The optical material may be treated to include light filtering properties for absorbing specific wavelengths of light, or other known treatment to obtain the desired optical properties. It is preferred for safety purposes that the contact element be made of ophthalmic plastic, such as poly methyl methacrylate or cr-39, and that the biconvex aspheric anterior element be made of optical glass, such as Schott BK7.

The aspheric contact element is mounted in the small end of the housing unit 12 so as to extend outwardly therefrom to enable contacting with the eye. The biconvex aspheric anterior element is mounted in the larger diameter end of housing 1 inwardly of the open end to protect the lens. Both surfaces of the biconvex aspheric anterior element and the anterior surface of the aspheric contact element may be coated with an anti-reflective coating to minimize reflections and increase light transmission. The contact element may be secured in place with optical glue, by means of interlocking threads, or by other conventional means. The interior portion of the larger diameter end of the conically shaped housing includes a generally cylindrical portion 20 which is approximately 0.003" larger in diameter than the diameter of the biconvex aspheric lens. The portion 20 provides a cylindrical cavity into which the biconvex aspheric lens 16 may be fitted and with a secondary cylindrical inner diameter 22, approximately 0.040" smaller than the diameter of the biconvex aspheric lens, providing a shoulder on which the outer edge of the aspheric biconvex lens 16 is supported and spaced from the aspheric contact element. The depth of the primary cylinder is adequate to provide protection for the anterior surface of the biconvex aspheric lens when affixed against the secondary cylindrical shoulder. The primary cylinder may be internally threaded at 24 to receive an externally threaded retaining ring 26 securing the biconvex aspheric lens in place against the secondary cylindrical shoulder 22. The threaded retaining ring systems are standard conventional means by which optical lenses are secured in lens housings.

In the preferred embodiment of the invention, the contact element 14 and anterior element 16 both have positive refractive power and act in conjunction with one another to produce an extremely wide field of view of the fundus of an eye which is substantially free of optical aberrations. Additionally, the biconvex aspheric anterior element 16 is designed to coact with the plus powered contact element in such a way as to produce a condensing lens system for projection of light from a biomicroscope light source to produce a clear image of the light source aperture on the fundus of the eye. In the image forming function of the lens system 10, with light rays 28, 29 and 30 originating at and diverging from points 31, 32 and 33 respectively on the eye fundus 34 exit the eye through the pupil 36 and cornea 38 and are caused to converge by the aspheric contact element 14 towards the biconvex aspheric element 16 which additionally converges the rays to focus at image plane 40 anterior to the biconvex element 16.

Turning now to FIG. 2, the light ray paths of the illumination system of a conventional slit lamp biomicroscope when used in conjunction with the lens system of the present invention are shown. As mentioned earlier, the lens system of this invention has been designed to perform in an optimal fashion as a condensing lens for projecting a clear, sharply focused image of the aperture of the light source of a biomicroscope onto the fundus of an examined eye. In FIG. 2, light rays 50, 51 and 52 originating at a light source filament 53 are refracted by a condenser lens assembly 54 which directs the light rays towards the slit lamp aperture 56 which is situated at the back focus plane of condenser lens system 58. Functioning as a new light source at slit lamp aperture 56, light rays 60, 61 and 62 proceed toward and are refracted by condenser lens system 58 and continue toward mirror 64 which reflects the light rays at approximately 45 degrees towards the image plane 40 where the light rays form an aerial image of the slit lamp aperture 56. The image plane 40 functions as a new light source wherein light rays 68, 69 and 70 proceed to and are refracted by the aspheric biconvex lens 16. The aspheric biconvex lens being a plus powered lens causes the light rays 68, 69 and 70 to converge towards the aspheric contact element 14 of the device. The contact element is also plus powered and causes the light rays to further converge toward the pupil 36 of the examined eye through the cornea 38. The light rays proceed through the eye and are focused as a clear image of the slit lamp aperture 56 onto the fundus of the examined eye 34 at points 72, 74 and 76.

The condensing qualities of the lens system of the invention operate to transmit light rays from the light source onto the fundus of the eye without incurring optical aberrations which may be caused by typical lens systems. The plus powered meniscus aspheric contact element as well as a plus powered biconvex aspheric anterior element each contribute positive refractive power to the optical system and coact with one another in such a way to provide optimum condensing and image forming properties. The lens system provides significant light converging properties along with aspheric surfaces which optimize the optical system to avoid aberrations especially at the periphery of the formed image. The lens system also enables an extremely wide field of view and illumination so as to avoid the use of transillumination techniques or the like.

One of the novel features of this invention relates to the aspheric design of the contact element, where either the convex only or both the concave and convex surfaces are aspheric. The aspheric surfaces of revolution are of prolate type, decreasing in curvature from apex to periphery, and each of the two surfaces are on a common axis of revolution. An additional novel feature of this invention relates to the aspheric design of the biconvex element, where both the posterior and anterior surfaces are defined by the polynomial:

$$y=(2rx+(e^2-1)x^2)^{\frac{1}{2}}+Ax^F+Bx^G+Cx^H.$$

The values of r, e, A, B, C, F, G, and H are chosen such that light rays originating at the fundus 34 of the eye, exiting through the pupil 36 of the eye and passing through the aspheric contact element 14 and biconvex aspheric element 16 form an aerial image of the fundus of the eye anterior to the aspheric biconvex element 16 at plane 40. The image is substantially free of aberrations such as field curvature, lateral astigmatism, and distortion.

In the preferred embodiment, the apical radius of curvature for each surface of the biconvex aspheric element 16 may range from 70 mm to 5 mm and may be in a reciprocal relationship with the apical radius of curvature of the opposite surface of element 16, ranging from 0.588 to 1.7 times its opposite surface radius value. For both front and back surfaces, values of e, representing apical eccentricity, may range from 0.7 to 4.0, coefficients A, B, C may range from −10.0 to 10.0, and exponents F, G, and H may range from 0.5 to 10.0. By selecting an anterior to posterior apical radius of curvature relationship of 1.6 to 1, and with the anterior surface polynomial utilizing the following parameters: r=9.887, e=1.3, A=0.022, B=−0.05, C=0.008, F=1.4, G=1.65, H=1.8, and with the posterior surface polynomial utilizing the following parameters: r=14.8305, e=2.6, A=−0.0210, B=0.028, C=−0.0118, F=1.4, G=1.65, H=1.8, the surfaces produced result in a biconvex element design ideal for contributing optimum condensing and image forming qualities to the lens system.

In the preferred embodiment, the contact element 14 has positive refractive power making it desirable to aspherize its convex anterior surface in order to minimize excess peripheral power and associated optical aberrations. The contact element 12 thereby aids the biconvex aspheric lens 14 in producing an aerial image free of aberrations. Additionally, the concave posterior surface of the contact lens 12 may be aspherized to closely approximate the aspheric corneal contour, with an apical radius of curvature substantially the same as that of the anterior surface of the average cornea. If the concave posterior surface is aspherized, it may be desirable to provide a peripheral slope of the lens which is equal to or less than that of the average cornea at an equivalent diameter, thereby minimizing the possibility of localized peripheral lens bearing and facilitating translational movement of the lens on the cornea. By having both surfaces of the contact element 12 aspheric, the beneficial optical properties resulting from aspherizing each surface are combined together.

Both the posterior and anterior surface curvatures of the contact element may be defined by the same polynomial:

$$Y=(2rx+(e^2-1)x^2)^{\frac{1}{2}}+Ax^F+Bx^G+Cx^H$$

where, for the convex anterior surface, values of r, e, A, B, C, F, G and H are chosen to satisfy optical correction based on the total refractive power of the contact element and the corresponding values of r, e, A, B, C, F, G, and H of the posterior concave surface. For the convex anterior surface, the apical radius of curvature, r, may range from 3.5 to 9.0, and e, representing apical eccentricity, may range from 0.05 to 1.4, coefficients A, B, and C may range from −10.0 to 10.0 and exponents F, G, and H may range from 0.5 to 10. For the concave posterior surface, the apical radius of curvature, r, may range from 6.5 to 9.0, and e, representing apical eccentricity may range from 0.0 to 1.2, coefficients A, B, C may range from −10.0 to 10.0 and exponents F, G, and H may range from 0.5 to 10. With the following parameters utilized for the convex anterior surface, r=6.9, e=0.685, A=−0.011, B=0.017, C=−0.0035, F=1.6, G=1.85, H=2.4, and the following parameters utilized for the concave posterior surface r=7.7, e=0.55, A=0.023, B=−0.018, C=0.002, F=2.5, G=2.8, H=3.7, the surfaces produced result in a contact element design ideal for a lens constructed in accordance with this invention.

Assuming the values of r, e, A, B, C, F, G, and H of the above example for the concave posterior surface, a graph plotting the range of apical radii of curvature of the aspheric convex anterior surface against corresponding values of e, eccentricity, for the aspheric convex anterior surface is shown in FIG. 3. Corresponding values of A, B, C, F, G, and H for the range of values of r in 0.4 mm increments are shown Table I below.

TABLE I

| Apical Radius of Curvature | Constant Coefficients | | | Constant Exponents | | |
|---|---|---|---|---|---|---|
| | A | B | C | F | G | H |
| 6.9 | −.011 | .017 | −.0035 | 1.6 | 1.85 | 2.4 |
| 6.5 | −.0116 | .0177 | −.00403 | 1.5872 | 1.8372 | 2.3615 |
| 6.1 | −.0123 | .01848 | −.00462 | 1.5730 | 1.8231 | 2.3192 |
| 5.7 | −.01305 | .0193 | −.0052 | 1.559 | 1.809 | 2.2769 |
| 5.3 | −.014 | .0203 | −.006 | 1.54 | 1.79 | 2.219 |
| 4.9 | −.0151 | .0215 | −.0069 | 1.518 | 1.768 | 2.154 |
| 4.5 | −.0166 | .02313 | −.00813 | 1.4885 | 1.738 | 2.065 |
| 4.1 | −.01805 | .02476 | −.00935 | 1.459 | 1.709 | 1.9769 |
| 3.7 | −.01997 | .02687 | −.01095 | 1.4205 | 1.670 | 1.8615 |
| 3.5 | −.021 | .02801 | −.0118 | 1.4 | 1.65 | 1.8 |

The diameter of the convex anterior surface may range from 6 to 16 mm, while the diameter of the concave posterior surface may be varied, and is most preferably around 12.0 mm. A peripheral portion of the contact element on the concave posterior surface may include a secondary peripheral curvature and overall may be as large as 17 mm, with a diameter of 15.5 mm being preferred. Center thickness of the contact element may range from 1.5 mm to 10 mm.

Figure 4:
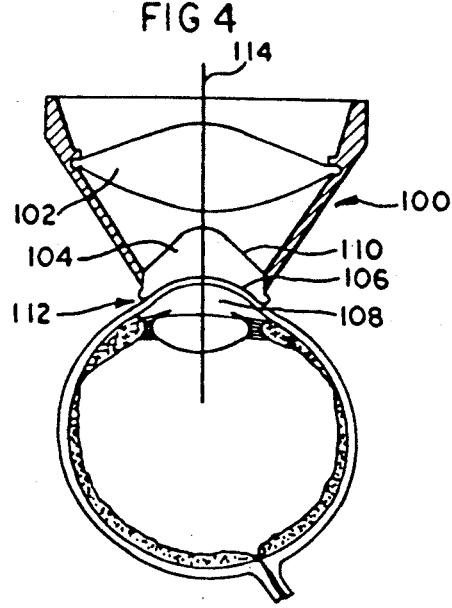
FIGS. 4 and 5 show translational movement of the lens system on an examined eye.
Figure 5:
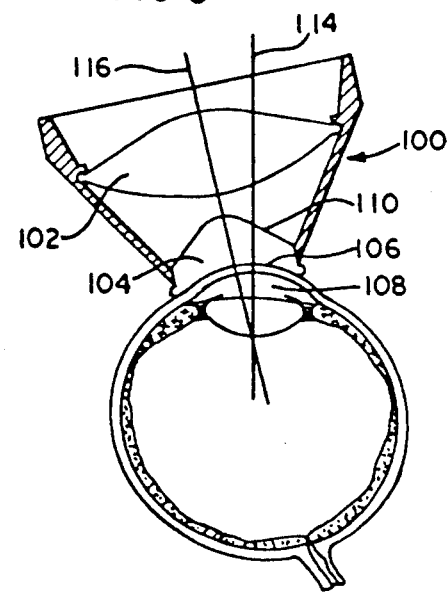

Turning now to FIGS. 4 and 5, an alternate embodiment of the design of the contact element is shown which facilitates translational movement of the lens on the cornea of the examined eye and provides additional advantages. In FIG. 4, the device 100 includes an anterior lens element 102 and contact element 104 which is designed having an aspheric posterior concave surface 106. The concave posterior surface 10 of the contact element 104 is designed to closely approximate the aspheric contour of the cornea 108 of the examined eye over most of its surface. The concave posterior surface 106 of the contact element 104 is of prolate type, wherein the curvature decreases from the apex to the periphery of the lens. As seen at 112, it may be desirable to progressively flatten the peripheral slope of the surface so as to be equal or less than that of the average cornea at an equivalent diameter. By forming the surface in this manner, the device 100 functions as previously described to provide a condensing lens system for transmitting light from a light source onto the fundus of an eye as well as forming an aberration free, wide field image of the fundus when the device is on axis with the cornea of the eye at 114.

Additionally, the aspheric contact surface of the contact element 104 allows translational movement of the device 100 on the cornea surface with minimum localized peripheral lens bearing on the cornea. As seen in FIG. 5, translational movement of the device 100 to axis 116 is possible without incurring excessive localized lens bearing on the corneal surface 108 of the examined eye. It is also seen that the aspheric surface 106 generally maintains close contact with the cornea 108 throughout translational movement. The aspheric surface 106 of the contact element 104 will also function to inhibit the retention of bubbles between the contact element and the cornea of the eye which is a common problem in existing lens systems.

The diagnostic contact lens system for indirect ophthalmoscopy of the invention provides an optically superior condensing lens system and image forming system. The use of positive powered lens elements in the system as well as aspheric surfaces of revolution result in substantial correction of optical aberrations, lateral astigmatism and field curvature in an easily used, effective system. Although preferred embodiments of the invention have been described, it is to be understood that various modifications would be obvious to those skilled in the art and are embodied within the present invention as defined by the appended claims.

What is claimed is:

1. An indirect ophthalmoscopy device used to observe the fundus of the eye comprising,
   a holding means to support and position a plurality of lenses relative to one another,
   said plurality of lenses including a contact lens element having a concave posterior surface and convex anterior surface, wherein said anterior surface is an aspheric surface of revolution having continuous and progressive variation in curvature peripheralward, said anterior surface being non-spherical over its extent, and
   at least one anterior lens element having first and second convex surfaces wherein said first and second convex surfaces are surfaces of revolution,
   said contact element and at least one anterior element being positioned relative to one another and acting in conjunction with one another to refract light rays from a biomicroscope illumination system to form a sharply defined and distortion free image of the biomicroscope light source aperture onto the fundus of an examined eye and to collect light rays emerging from the fundus of the eye and refracting said emerging light rays to form an aerial image of the fundus anterior to said at least one anterior element with said image being substantially free of optical aberrations.

2. The indirect ophthalmoscopy contact lens of claim 1 wherein,
   said concave posterior surface of said contact element is an aspheric surface of revolution which is substantially the shape of the anterior surface of the cornea of the eye to which the contact element is applied.

3. The indirect ophthalmoscopy contact lens of claim 1 wherein,
said anterior surface of said contact element has an apical radius of curvature in the range from 3.5 mm to 9.0 mm and has a diameter in the range from 6.0 mm to 16.0 mm.

4. The indirect ophthalmoscopy contact lens of claim 1 wherein,
said anterior surface of said contact element has an apical eccentricity in the range from 0.05 to 1.4.

5. The indirect ophthalmoscopy contact lens of claim 1 wherein,
at least one of said first and second convex surfaces of said at least one anterior lens element is an aspheric of revolution and have an apical radius of curvature in the range from 5.00 mm to 70.0 mm and an apical eccentricity in the range from 0.7 to 4.0 eccentricity units.

6. The indirect ophthalmoscopy contact lens of claim 5 wherein,
the apical radius of curvature for each of the first and second convex surfaces of said at least one anterior lens element form a reciprocal relationship with each other ranging from 0.588 to 1.7 times the apical radius of curvature of the opposite surface of said anterior lens element.

7. The indirect ophthalmoscopy device of claim 1 wherein,
said contact lens element has positive refractive power, and said aspheric surface of revolution of said contact element minimizes excess peripheral power and optical aberrations generated due to the positive refractive power of said contact element.

8. The indirect ophthalmoscopy device of claim 1 wherein,
said aspheric anterior surface of said contact element is defined by the polynomial expressed as follows:

$$Y = (2rx + (e^2 - 1)x^2)^{\frac{1}{2}} + Ax^F + Bx^G + Cx^H$$

where r is the apical radius of curvature, e is the apical eccentricity, x is the distance from the apex of the surface along its axis of revolution, and A, B and C are constant coefficients, and F, G and H are constant exponents wherein the values of apical radius, apical eccentricity, the coefficients and exponents for the aspheric surfaces of said contact element and said anterior element are chosen to produce an image of the fundus of the eye free of field curvature, lateral astigmatism, and optical aberration.

9. The indirect ophthalmoscopy contact lens of claim 8 wherein,
said convex anterior surface of said contact element has an apical radius of curvature, r, in the range from 3.5 mm to 9.0 mm, an apical eccentricity, e, in the range from 0.05 to 1.4, coefficients A, B and C range from −10 to 10 and exponents F, G and H range from 0.5 to 10 wherein based upon the total refractive power of said contact element, these values will satisfy optical correction at the center and periphery of said contact element.

10. The indirect ophthalmoscopy contact lens of claim 8, wherein,
said concave posterior surface of said contact element is an aspheric surface of revolution defined by said polynomial and having an apical radius of curvature, r, in the range from about 6.5 mm to 9.0 mm, an apical eccentricity, e, in the range from 0.0 to 1.2, coefficients A, B and C in the range from −10 to 10 and exponents F, G and H in the range from 0.5 to 10 wherein r, e, A, B, C, F, G, and H are chosen to cause said posterior surface to substantially conform tot he shape of the anterior surface of the cornea of the eye to which said contact element is to be applied and to eliminate localized peripheral lens bearing during translational movement on said cornea.

11. The indirect ophthalmoscopy device of claim 1 wherein,
said at least one anterior element has at least one aspheric surface of revolution with said aspheric surface defined by the polynomial expressed as follows:

$$Y = (2rx + (e^2 - 1)x^2)^{\frac{1}{2}} + Ax^F + Bx^G + Cx^H$$

where r is the apical radius of curvature, e is the apical eccentricity, x is the distance from the apex of the surface along its axis of revolution, and A, B and C are constant coefficients, and F, G and H are constant exponents, wherein said aspheric surface of said anterior element has an apical radius of curvature, r, in the range from 5.0 mm to 70.0 mm, apical eccentricity, e, in the range from 0.7 to 4.0, coefficients A, B and C in the range from −10 to 10, and exponents F, G and H in the range from 0.5 to 10 wherein the generated surfaces are designed to provide optimum fundus image forming qualities in conjunction with said contact element as well as projecting a clear and aberration free image of a biomicroscope light source aperture on the fundus of the eye.

12. An indirect ophthalmoscopy device used to observe the fundus of the eye comprising,
a holding means to support and position a plurality of lenses relative to one another,
said plurality of lenses including a contact lens element having a concave posterior surface and convex anterior surface, wherein said posterior surface is an aspheric surface of revolution having a continuous and progressive reduction in curvature peripheralward with said posterior surface having a peripheral slope equal to or less than that of an average cornea at an equivalent diameter thereby minimizing localized peripheral lens bearing during translational movement of said contact element on the cornea, and
at least one anterior lens element having positive refractive power and first and second convex surfaces wherein said first and second convex surfaces are surfaces of revolution,
said contact element and at least one anterior element being positioned relative to one another and acting in conjunction with one another to refract light rays from a biomicroscope illumination system to form a sharply defined and distortion free image of the biomicroscope light source aperture onto the fundus of an examined eye and to collect light rays emerging from the fundus of the eye and refracting said emerging light rays to form an aerial image of the fundus anterior to said at least one anterior element with said image being substantially free of optical aberrations.

13. A device for observing the fundus of the eye under applied illumination comprising, a contact lens element having a convex anterior surface and a concave posterior surface, at least one anterior lens element positioned relative to said contact lens element, having at least one convex surface being an aspheric surface of revolution, with said aspheric surface being non-conoid and defined by the polynomial expressed as follows:

$$Y=(2rx+(e^2-1)x^2)^{\frac{1}{2}}+Ax^F+Bx^G+Cx^H$$

where r is the apical radius of curvature, e is the apical eccentricity, x is the distance from the apex of the surface along its axis of revolution, and A, B and C are constant coefficients, and F, G and H are constant exponents for the aspheric surfaces of said anterior element, a holding means supporting said contact and anterior lens elements relative to one another, wherein light rays projected from a light source are converged through the device onto the fundus of the eye and emerge from the fundus to be refracted by the device to form an image of the fundus substantially free of optical aberrations.

14. The device of claim 13 wherein,
said at least one anterior lens element has positive refractive power which in conjunction with said contact element yield significant light converging properties and produce an extremely wide field of view of the fundus of the eye.

15. The indirect ophthalmoscopy device of claim 13 wherein,
said at least one convex surface of said at least one anterior lens element has an apical radius of curvature, r, in the range from 5.0 mm to 70.0 mm, apical eccentricity, e, in the range from 0.7 to 4.0, coefficients A, B and C in the range from −10 to 10, and exponents F, G and H in the range from 0.5 to 10, wherein the generated surfaces are designed to provide optimum fundus image forming qualities in conjunction with said contact element as well as projecting a clear and aberration free image of a biomicroscope light source aperture on the fundus of the eye.

16. An indirect ophthalmoscopy contact lens system, comprising,
a contact lens element having a convex anterior surface and a concave posterior surface, wherein said anterior surface is an aspheric surface of revolution, at least one anterior lens element positioned relative to said contact lens element by a holding means supporting said contact and said at least one anterior lens elements relative to one another wherein said at least one anterior lens element has first and second surfaces, wherein said anterior surface of said contact lens element and said first and second surfaces of at least one of said at least one anterior lens element are surfaces of revolution defined by the polynomial expressed as follows:

$$Y=(2rx+(e^2-1)x^2)^{\frac{1}{2}}+Ax^F+Bx^G+Cx^H$$

where r is the apical radius of curvature, e is the apical eccentricity, x is the distance form the apex of the surface along its axis of revolution, and A, B and C are constant coefficients, and F, G and H are constant exponents wherein the values of r, e, A, B, C, F, G and H are chosen to produce an image of the fundus of the eye free of field curvature, lateral astigmatism, and optical aberrations.

17. The indirect ophthalmoscopy contact lens system of claim 16, wherein,
at least one of said first and second surfaces of said anterior element is an aspherical surface of revolution, and having an apical radius of curvature, r, in the range from 5.0 mm to 70.0 mm, apical eccentricity, e, in the range from 0.7 to 4.0, coefficients A, B and C in the range from −10 to 10, and exponents F, G and H in the range from 0.5 to 10, wherein the generated surfaces are designed to provide optimum fundus image forming qualities in conjunction with said contact element as well as projecting a clear and aberration free image of a biomicroscope light source aperture on the fundus of the eye.

18. The indirect ophthalmoscopy contact lens system of claim 16, wherein,
said concave posterior surface of said contact element is an aspherical surface of revolution which has a continuous and progressive reduction in curvature peripheralward with a peripheral slope equal to or less than that of an averaged cornea at an equivalent diameter thereby minimizing localized peripheral lens bearing during transnational movement of said contact element on the cornea.

19. The indirect ophthalmoscopy contact lens system of claim 16, wherein,
said convex anterior surface of said contact element is an aspherical surface of revolution having a continuous and progressive reduction in curvature peripheralward, and has an apical radius of curvature, r in the range from 3.5 mm to 9.0 mm, an apical eccentricity, e, in the range from 0.05 to 1.4, coefficients A, B and C range from −10 to 10 and exponents F, G and H range from 0.5 to 10 wherein these values are chosen to satisfy optical correction at the center and periphery of said contact element.

20. The indirect ophthalmoscopy contact lens system of claim 16, wherein,
at least one of said contact element or at least one anterior element has positive refractive power thereby minimizing excess peripheral power and optical aberrations.

* * * * *